(12) United States Patent
Weber et al.

(10) Patent No.: US 9,844,405 B2
(45) Date of Patent: Dec. 19, 2017

(54) METHOD AND APPARATUS FOR MONITORING AND ABLATING NERVES (71) Applicant: Cardiac Pacemakers, Inc., St. Paul, MN (US)

(72) Inventors: Jan Weber, Maastricht (NL); Torsten Scheuermann, Munich (DE); Roger Hastings, Maple Grove, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 466 days.

(21) Appl. No.: 13/720,514

(22) Filed: Dec. 19, 2012

(65) Prior Publication Data

US 2014/0073903 A1 Mar. 13, 2014

Related U.S. Application Data (60) Provisional application No. 61/577,890, filed on Dec. 20, 2011.

(51) Int. Cl.
| | | |
|---|---|---|
| *A61B 5/05* | (2006.01) | |
| *A61B 18/12* | (2006.01) | |
| *A61B 5/04* | (2006.01) | |
| *A61B 5/00* | (2006.01) | |
| *A61B 18/14* | (2006.01) | |
| *A61B 18/00* | (2006.01) | |
| *A61N 7/02* | (2006.01) | |
| *A61B 18/18* | (2006.01) | |
| *A61B 90/00* | (2016.01) | |

(52) U.S. Cl.
CPC ........ *A61B 18/1233* (2013.01); *A61B 5/0059* (2013.01); *A61B 5/04009* (2013.01); *A61B 5/05* (2013.01); *A61B 5/40* (2013.01); *A61B 5/6852* (2013.01); *A61B 18/1206* (2013.01); *A61B 18/1492* (2013.01); *A61B 2018/00404* (2013.01); *A61B 2018/00434* (2013.01); *A61B 2018/00511* (2013.01); *A61B 2018/00577* (2013.01); *A61B 2018/00839* (2013.01); *A61B 2018/00994* (2013.01); *A61B 2018/1273* (2013.01); *A61B 2018/1861* (2013.01); *A61B 2090/3966* (2016.02); *A61N 7/022* (2013.01)

(58) Field of Classification Search
None
See application file for complete search history.

(56) References Cited

U.S. PATENT DOCUMENTS 4,587,487 A * 5/1986 Zanzucchi ................ 324/244.1
5,767,976 A * 6/1998 Ankerhold et al. .......... 356/437
6,185,448 B1 2/2001 Borovsky
(Continued)

OTHER PUBLICATIONS

Skidmore et al. (US 2010/0219820; hereinafter Skidmore) and Perez et al. ("Rubidium vapor cell with integrated nonmetallic multilayer reflectors"; IEEE; Jan. 13-17, 2008).*
(Continued)

*Primary Examiner* — Amanda Lauritzen Moher
*Assistant Examiner* — Shahdeep Mohammed (57) ABSTRACT

Described is an apparatus for locally monitoring nerve activity that may be incorporated into a nerve ablation catheter. Such a catheter is equipped with magnetic sensing for both identifying nerves and assessing the success of the ablation. The catheter is also equipped with an ablation instrument for both stimulating and destroying nerve tissue.

26 Claims, 6 Drawing Sheets

(56) References Cited

U.S. PATENT DOCUMENTS

| | | | |
|---|---|---|---|
| 7,826,065 B1* | 11/2010 | Okandan et al. | 356/521 |
| 9,167,979 B2 | 10/2015 | Skidmore et al. | |
| 2005/0288730 A1 | 12/2005 | Deem et al. | |
| 2006/0178698 A1* | 8/2006 | McIntyre et al. | 606/200 |
| 2006/0293649 A1* | 12/2006 | Lorang | A61B 18/1206 |
| | | | 606/32 |
| 2007/0167723 A1* | 7/2007 | Park et al. | 600/409 |
| 2010/0219820 A1* | 9/2010 | Skidmore et al. | 324/247 |
| 2012/0172727 A1 | 7/2012 | Hastings et al. | |

OTHER PUBLICATIONS

Wijesinghe ("Magnetic measurements of peripheral nerve function using a neuromagnetic current probe"; Experimental Biology and Medicine 2010; 235: 159-169).*

"Anatomy", [Online]. Retrieved from the Internet: <URL:http://upload.wikimedia.org/wikipedia/commons/2/2d/Gray847.png>, (Dec. 11, 2012 accessed), 1 pg.

Bison, G., et al., "Dynamical mapping of the human cardiomagnetic field with a room-temperature, laser-optical sensor", Optics Express, 11(8), (2003), 904-909.

Hertzberg, Y., et al., "Towards multifocal ultrasonic neural stimulation: pattern generation algorithms", J Neural Eng., 7(5), (Oct. 2010), 056002.

Honda, M., et al., "Nanoscale heating of laser irradiated single gold nanoparticles in liquid", Opt Express., 19(13), (Jun. 20, 2011), 12375-83.

Karpa, Leon, et al., "Frequency Matching in Light-Storage Spectroscopy of Atomic Raman Transitions", Phys. Rev. Lett., 103, (2009), 093601 (4 pgs.).

Koch, H., "Squid magnetocardiography: status and perspectives", IEEE Transactions on Applied Superconductivity, 11(1), (2001), 49-59.

Liew, Li-Anne, et al., "Microfabricated alkali atom vapor cells", Applied Physics Letters, 84(14), (2004), 2694-2696.

Perez, M. A, et al., "Rubidium vapor cell with integrated nonmetallic multilayer reflectors", IEEE 21st International Conference on Micro Electro Mechanical Systems, 2008. MEMS 2008., (2008), 790-793.

Richardson, Leonard B., et al., "Integrated Ultrasound Ablation and Imaging Device and Related Methods", U.S. Appl. No. 13/676,871, filed Nov. 14, 2012.

Roth, B. J., et al., "Using a magnetometer to image a two-dimensional current distribution", J. Appl. Phys., 65, (1989), 361-372.

Schwindt, Peter, et al., "Chip-scale atomic magnetometer", Applied Physics Letters, 85(26), (2004), 6409-6411.

Weis, A., et al., "Mapping of Human Heart Beat Dynamics by Atomic Magnetometers", AIP Conf. Proc. 770, Atomic Physics 19: XIX International Conference on Atomic Physics; ICAP 2004, (2004), 373-380.

Wells, J., et al., "Biophysical mechanisms of transient optical stimulation of peripheral nerve.", Biophys J., 93(7), (Oct. 1, 2007), 2567-80.

Wijesinghe, R. S, "Magnetic measurements of peripheral nerve function using a neuromagnetic current probe", Exp Biol Med, 235(2), (Feb. 2010), 159-69.

Wininger, Fred A, et al., "Complete Optical Neurophysiology: Toward Optical Stimulation and Recording of Neural Tissue", Applied Optics, 48(10), (2009), D218-D224.

Wu, Bin, et al., "Planar Hollow-Core Waveguide Technology for Atomic Spectroscopy and Quantum Interference in Alkali Vapors", Journal of Lightwave Technology, 26(23), (2008), 3727-3733.

Xia, H., "Magnetoencephalography with an atomic magnetometer", Applied Physics Letters, 89(21), (Nov. 2006), 211104-1-211104-3.

* cited by examiner

METHOD AND APPARATUS FOR MONITORING AND ABLATING NERVES

CLAIM OF PRIORITY

This application claims the benefit of priority under 35 U.S.C. §119(e) of Weber et al., U.S. Provisional Patent Application Ser. No. 61/577,890, entitled "METHOD AND APPARATUS FOR MONITORING AND ABLATING NERVES", filed on Dec. 20, 2010, which is herein incorporated by reference in its entirety.

BACKGROUND

Numerous medical procedures are performed today that involve the purposeful destruction of selected nervous tissue for therapeutic effect. Such procedures may be performed on nerves that are causing pain or other undesired physiological effects such as abnormal autonomic activity. For purposes of pain management, for example, nerve ablation procedures are commonly performed on peripheral, spinal, or pelvic nerves.

A specific example of a physiological consequence of abnormal autonomic activity is hypertension. The sympathetic nervous system plays an important role in circulatory and metabolic control and is a major contributor to the development of hypertension. One pathway by which elevated sympathetic nerve activity initiates and sustains the elevation of blood pressure is via the kidneys. Increased sympathetic outflow to the kidneys via sympathetic efferent nerves leads to both acute and long-term blood pressure elevations due to increased sodium and water retention, increased renin release, and alterations of renal blood flow-effects. Signals from renal afferent sympathetic nerves are also believed to contribute to hypertension by acting on the brain to increase sympathetic drive. Adequate renal function is not dependent on these nerves, as evidenced by patients who undergo transplantation with denervated kidneys and survive without complications. Catheter-based renal sympathetic nerve ablation has been shown to be a viable therapeutic approach for the treatment of hypertension in certain patients. In this procedure, an intravascular catheter with an ablating instrument is introduced into the renal artery. The renal plexus is a network of nerve fibers located around the renal artery, primarily in the adventitia, and contains post-ganglionic fibers from the sympathetic nervous system as well as sympathetic afferents. The nerve fibers from the plexus enter the kidney with the branches of the renal artery. Applying RF (radio-frequency) energy from the ablating instrument to these nerves effectively denervates the kidney to prevent the sympathetic mechanisms described above from contributing to a patient's hypertension.

DETAILED DESCRIPTION

In a nerve ablation procedure, such as for renal nerve ablation, it would be useful to be able to monitor nerve activity in order to more accurately perform the procedure and to verify that the procedure was successful. Besides aiding in nerve ablation procedures, localized monitoring of nerve activity may also be useful in diagnosing disease or injury of nerves and in assessing the efficacy of various therapeutic procedures and agents. Described herein are methods and apparatus for localized monitoring of and/or performing ablation procedures on nervous tissue.

In one embodiment, an apparatus for ablation of selected nervous tissue comprises: a catheter that comprises a tube having proximal and distal ends, an ablation instrument near the distal end of the catheter wherein the ablation instrument may be operated in a low-power stimulation mode to stimulate nervous tissue or may be operated in a high-power ablation mode to destroy nervous tissue, and a magnetic sensor near the distal end of the catheter wherein the magnetic sensor is configured to sense magnetic fields produced by nervous tissue as a result of stimulation by the ablation instrument. The catheter may be any kind of tube, flexible or otherwise, that is disposable in a body duct, cavity, or vessel in order to access the selected nervous tissue. The power levels of the ablation instrument for the low-power stimulation mode and the high-power ablation mode may be defined by a specified threshold power level, below which results in nerve cell stimulation and above which results in nerve cell necrosis. The threshold power level may be determined empirically as it would be expected to vary depending upon the where the procedure is performed and a patient's individual anatomy. In order to determine whether the stimulation resulted in nervous activity, the measured magnetic field may be correlated with the time at which the stimulation was delivered. An example technique for using the apparatus would include the following: disposing the ablation instrument and magnetic sensor adjacent the selected nervous tissue; attempting to stimulate the selected nervous tissue with the ablation instrument in stimulation mode; if the stimulation results in nervous activity as detected by the magnetic sensor, switching the ablation instrument to ablation mode to destroy the selected nervous tissue; and, if the stimulation does not produce detectable nervous activity, changing the location and/or orientation of the ablation instrument and repeating the procedure. The technique thus allows the delivery of ablation energy to be more precisely targeted than previous methods and also allows the success of the procedure in destroying nerve tissue to be evaluated as it is performed.

In another embodiment, an apparatus for locally monitoring nerve activity comprises: a vapor cell containing a sensor gas disposable adjacent selected nerve tissue; a mirror structure in the vapor cell; a laser source for generating light at selected frequencies; optical fiber for transmitting light from the laser source to the vapor cell and receiving light reflected therefrom; circuitry for controlling the light transmission so that the vapor cell operates as a light-storage magnetometer with the reflected light having a frequency component that corresponds to the magnitude of the magnetic field at the location of the sensor gas; circuitry for processing the received light to measure the magnetic field at the location of the sensor gas; and, circuitry for analyzing the time course of the measured magnetic field to determine if the selected nervous tissue is active. The operating principles of such a light-storage magnetometer are described in more detail below. The vapor cell may be incorporated into a catheter with fiber optic cable running through one or more lumens of the catheter for transmitting and receiving light to and from the vapor cell. The sensor gas may be an element such as rubidium that needs to be heated so as to be in a vapor state. Light transmitted by the fiber optic cable may be used for this purpose where the vapor cell contains particles that are heated by the light. An example technique for monitoring nerve activity using this apparatus would comprise: disposing a vapor cell containing a sensor gas adjacent selected nerve tissue; transmitting light to the vapor cell and receiving light reflected therefrom; controlling the light transmission so that the vapor cell operates as a light-storage magnetometer with the reflected light having a frequency component that corresponds to the magnitude of the magnetic field at the location of the sensor gas; processing the received light to measure the magnetic field at the location of the sensor gas; and, analyzing the time course of the measured magnetic field to determine if the selected nervous tissue is active. The apparatus may also be incorporated into a nerve ablation catheter as described above and used as the magnetic sensor for determining if stimulation energy from the ablation instrument results in activity of the selected nervous tissue. The apparatus may include circuitry for generating a magnetic sensor waveform and detecting a change in the magnetic sensor waveform that is time-correlated with the actuation of the ablation instrument in low-power mode Further embodiments of an ablation catheter and an apparatus for locally monitoring nerve activity are described in more detail below with reference to the specific example of renal nerve ablation. It should be appreciated that those embodiments could equally be employed for other types of nerve ablation and/or local monitoring of nerve activity.

Renal Nerve Ablation

There are significant problems associated with current intravascular ablation techniques for renal denervation. Although the catheter can be guided to the renal artery where the renal nerves are located, the direction of the ablation energy is imprecise. The ablation process therefore may kill not only renal nerves but also surrounding tissue. Also, the success of the ablation procedure cannot be evaluated during treatment so that a repeat of the procedure is sometimes necessary. In most current renal denervation procedures having no exact knowledge of the locations of the nerves, multiple locations are ablated at locations around the wall of the artery to kill the nerves. However, having specific knowledge about the location of the nerve bundles around the artery may result in being able to select ablation targets that are known to have nerves, or at least more likely to have nerves than arbitrary selection of an ablation target. This specific knowledge of nerve location may result in being able to ablate just at three or even two points, resulting in significant less damage to surrounding tissue. This specific knowledge may also result in more effective ablation of nerves, and more consistently effective therapy.

Described herein is a renal nerve ablation catheter equipped with a magnetic sensing for both identifying nerves and assessing the success of the ablation. The basic concept is to use the ablation instrument at a low power level that will stimulate, but not destroy, nervous tissue if the ablation energy is directed toward that tissue. Whether or not the ablation energy is directed toward nervous tissue surrounding the renal artery is determined with the magnetic sensor. The magnetic sensor is capable of detecting the magnetic field produced by nerve conduction. If a change in the detected magnetic field is detected that can be time-correlated with the application of the low-power stimulation energy, it may be surmised that the magnetic field change is due to nerve conduction caused by the stimulation energy. In order to improve reliability, testing for such a time-correlated magnetic field change may be repeated a selected number of times with the number of time-correlated changes compared with a specified threshold number. If the number of the changes exceeds the threshold, the ablation energy is assumed to be precisely targeted toward nerves surrounding the renal artery. After this testing, ablation energy is applied by the ablation instrument at a high-power level designed to kill nervous tissue. In order to determine whether or not the tissue was destroyed, the testing procedure as described above may be performed again without changing the location and orientation of the catheter. That is, low-power ablation energy is again applied, and if no time-correlated changes in the magnetic field are detected, it is assumed that the previously located nervous tissue has been ablated. These steps may be repeated after changing the location and/or orientation of the ablation instrument in order to adequately denervate the kidney.

Example Ablation Catheter and Therapeutic Procedure

Figure 1:
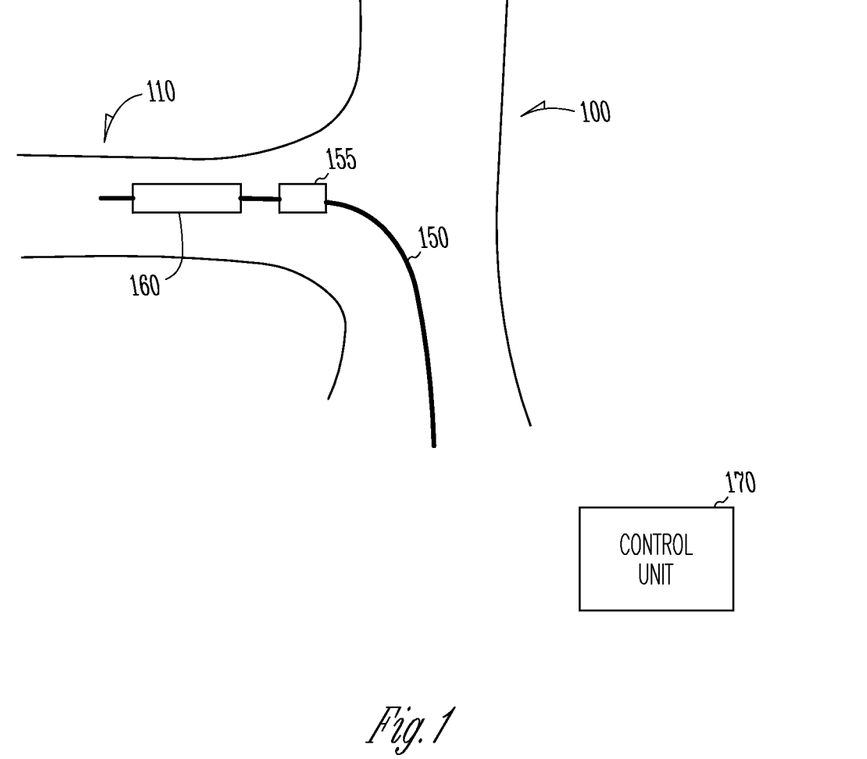
FIG. 1 illustrates a renal ablation catheter equipped with a magnetometer as the magnetic sensor.

An example embodiment of an apparatus for performing renal nerve ablation includes a catheter that comprises a flexible shaft or tubing having proximal and distal ends that may be intravascularly guided to the renal artery, an ablation instrument at the distal end of the catheter, and a magnetic sensor at the distal end of the catheter. The magnetic sensor is configured to sense magnetic fields near the renal nerves that may include the fields produced as a result of stimulation by the ablation instrument, and the ablation instrument may be operated in a high-power mode to destroy renal nerves or in a low-power mode to stimulate renal nerves. Such a renal ablation catheter equipped with a magnetometer as the magnetic sensor is shown in FIG. 1. The catheter 150 is shown located in the aorta 100 with its distal end disposed in the renal artery 110. The catheter 150 comprises a flexible shaft or tubing having proximal and distal ends, where the distal end may be intravascularly guided to the renal artery. At the distal end of the catheter is an ablation instrument 160 and a magnetic sensor or magnetometer 155. The proximal end of the catheter connects to a control unit 170 that contains the equipment for steering the catheter and the electronics for actuating the ablation instrument 160 and for receiving and analyzing the signals from the magnetometer 155. The ablation instrument of the catheter could apply energy in the form of electromagnetic radiation in various bands, such as the radiofrequency (RF) band (0.3 MHz-30 MHz), or the Super high frequency (or SHF) frequencies (RF) in the range of 3 GHz and 30 GHz used for microwave ablation, (laser) light, focused ultrasound, or a combination of different modalities. As noted above, conventional procedures use induced heat by electrical currents to destroy nerve bundles around the renal arteries. Heat can be also induced through ultrasound intended to be focused onto the nerves which are located outside of the artery 1-6 mm away from the inner surface (endothelium). High intensity ultrasound focused on deeper regions would help to avoid endothelium necroses, a disadvantage of other ablation techniques. The ablation instrument can have two modes: a nerve stimulating mode with lower energy where the energy is applied to cause local heating and expansion below the cell necrotizing temperature and a nerve ablation mode that causes local heating above the cell necrotizing temperature. As noted above, the power threshold for the two modes may be determined empirically. The magnetometer 155 is miniaturized as described below and can detect nerve activity through analyzing the generated B field around the nerve when the nerve conducts an impulse.

Figure 2:
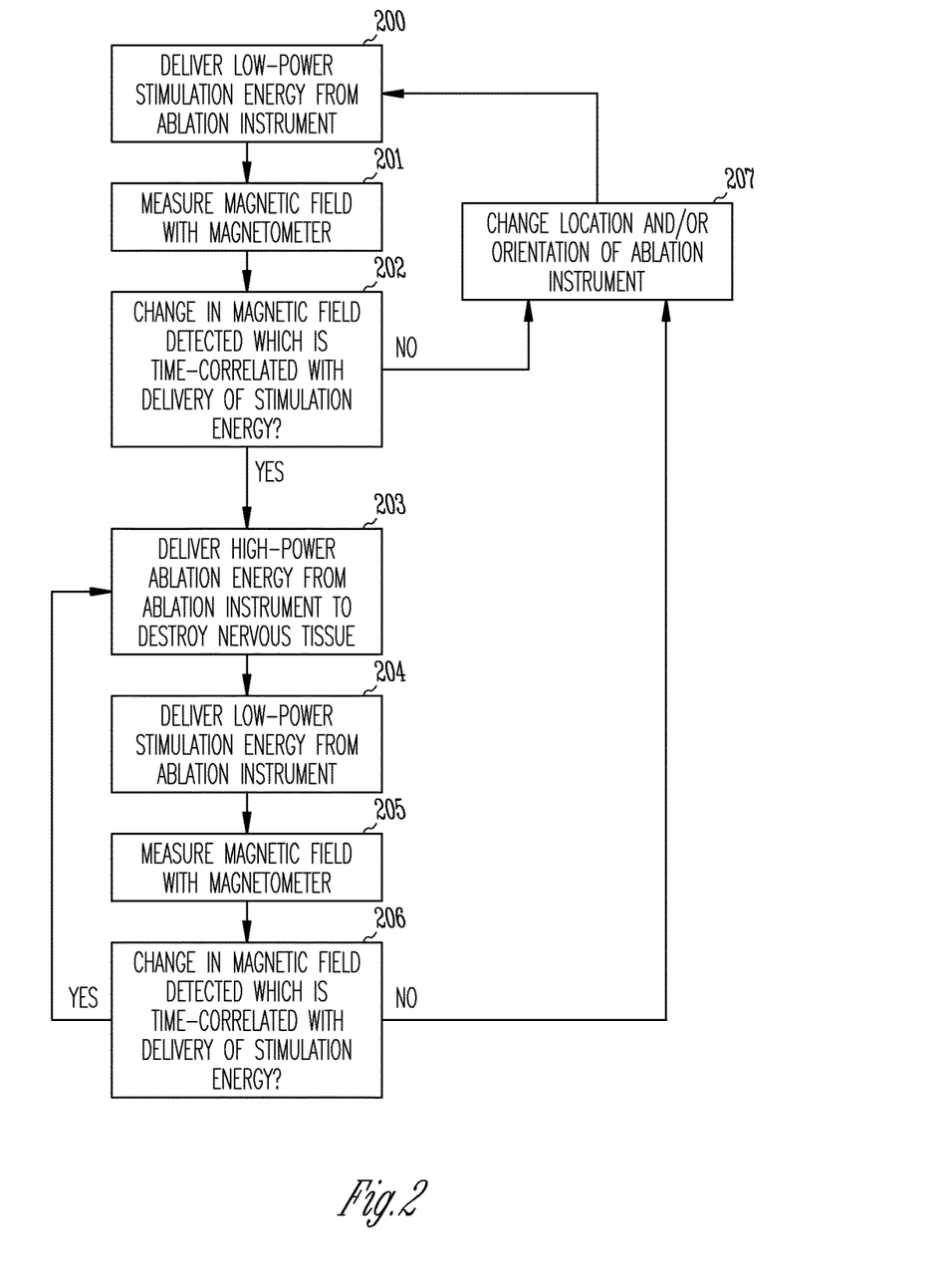
FIG. 2 illustrates the steps involved in performing a renal nerve ablation procedure according to one embodiment.

As explained above, nerve conduction signals brought about via stimulation by the ablation instrument can be detected in the magnetic field sensed by the magnetometer. If such nerve conduction is destroyed after application of high-power ablation energy, no correlation between the low-power stimulation signal and the measured magnetic signal occurs. FIG. 2 illustrates an example procedure. The ablation instrument is initially delivered into the renal artery and positioned at a location and orientation to ablate nervous tissue around the artery. At step 200, the ablation instrument is switched to a low-power stimulation mode and caused to deliver stimulation energy to the tissue surrounding the renal artery in a manner designed to stimulate nerves. Simultaneously with the delivery of the stimulation energy, the time course of the magnetic field is measured by the magnetometer at step 201. At step 202, the magnetometer signal over a defined time period is analyzed to determine if there is a change in the signal that is time-correlated with the application of stimulation energy. In certain embodiments, steps 200 through 202 are repeated a predetermined number of times to see if the time-correlated signal is detected for each stimulation (or a specified threshold number of stimulations) in order to lessen the probability of a false positive result. For example, a feature in the magnetometer signal that consistently occurs at the same time that the stimulation energy is delivered for a number of separate stimulations could be confidently judged to be due to nerve conduction caused by the stimulation energy. The control unit 170 may contain processing circuitry for analyzing the magnetometer signal waveform in order to detect a time-correlated change. If no time-correlated change is detected, the orientation and/or location of the ablation instrument, or for example the spatial orientation of the focused beam is changed at step 207 and the procedure returns to step 200. The focused beam can be changed in spatial direction by using two or more irradiative elements (ultrasound transducers or microwave antennas) and changing the relative phase between the two radiated waves. When the orientation and/or location of the ablation instrument is changed by moving the catheter, the magnetometer may be kept at its relative position to the nerve by sliding it in its guiding lumen opposite to the movement of the catheter. Such a guiding lumen for the magnetometer is illustrated in FIG. 3B as discussed below If a time-correlated change in the magnetic field is detected, the ablation instrument is switched to high-power mode, and ablation energy is delivered to the surrounding tissue at step 203. Subsequently, at step 204, the ablation instrument is switched to a low-power stimulation mode to deliver nerve stimulation energy, the magnetic field is monitored at step 205, and a time-correlated change in the magnetic field is looked for at step 206, similar to steps 200-202. Steps 204-206 are performed in order to verify that the nervous tissue has been adequately ablated. If no time-correlated signal in the magnetic field is detected, it may be assumed that the nervous tissue targeted by steps 200-202 has been destroyed. Steps 204-206 may be repeated a predetermined number of times to ensure that no time-correlated signal is detected before a final decision is reached. If a time-correlated signal is detected at step 206, the ablation is repeated by again performing steps 203-206, where these steps may be repeated as necessary or for only a predetermined number of times. If no time-correlated signal is detected at step 206, the orientation and/or location of the ablation catheter is changed at step 207 and the procedure begins again at step 200. The procedure may be performed in this manner until the kidney is denervated.

Figure 3A:
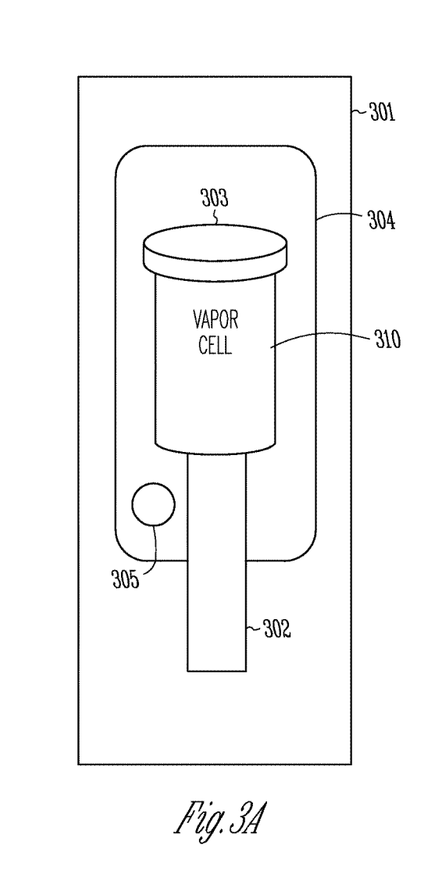
FIG. 3A shows a portion of the catheter tubing that contains the magnetometer or portions thereof.
Figure 3B:
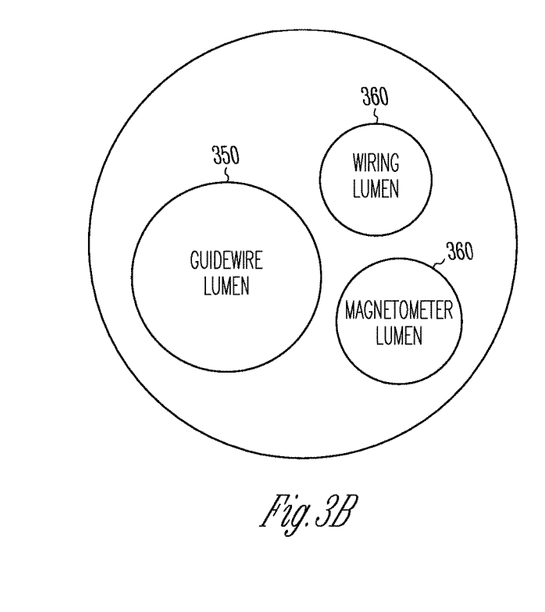
FIG. 3B shows the catheter tubing in cross-section.

FIGS. 3A and 3B depict the assembly of the magnetometer in the catheter according to one embodiment. As described in more detail below, the magnetometer may be an optical magnetometer which utilizes a gas contained within vapor cell for measuring the magnetic field. FIG. 3A shows a portion of the catheter tubing 301 that contains the magnetometer or portions thereof. The magnetometer includes a vapor cell 310 for containing the sensor gas (e.g., vaporized rubidium). The vapor cell 310 may also contain a buffer gas and be internally coated with paraffin for reducing the relaxation of polarized atoms within the cell due to collision with the cell walls. One or more optical fibers 302 connect to the vapor cell at one end, and a mirror layer 303 or other reflective construction is disposed at the other end of the vapor cell. As described below, the optical fiber 302 may be used to deliver energy for three purposes: optical pumping, probing, and heating. The vapor cell is shown as embedded in a structure 304 for isolating the tip of the magnetometer within the catheter tubing and for providing strain relief to the connection between the optical fiber and the vapor cell. The structure 304 may be, for example, an epoxy layer. In order for the magnetometer to be radiographically located in relation to the inside of the catheter, a marker 305 made of a heavy metal material with a very low permeability like gold can be included in the surrounding epoxy layer. The catheter tubing 301 may be pulled over the vapor cell and the light fiber. FIG. 3B shows the catheter tubing in cross-section that, in this example, includes a guidewire lumen 350, a lumen 360 for passing electrical wiring for actuating the ablation instrument as well as possibly receiving electrical signals, and a separate lumen 360 for the magnetometer.

Example Excitation/Ablation Source

The ablation instrument 160 may deliver energy in the form of RF, (laser) light, focused ultrasound, or a combination thereof. In one embodiment, an ultrasound beam may be directed in any line from the center of a catheter to a selected direction into the wall of an artery. For example, a disk shaped ultrasonic transducer may be 0.5, 1.0, or 1.5 mm in diameter, or other. The ultrasound beam has little attenuation as it passes through blood, but is attenuated in its passage through tissue. For example, a 10 MHz ultrasound beam travels about 6 mm into kidney tissue. The beam may be steered to any desired angle using a micro-motor. An array of ultrasound transducers along the catheter may further be used to focus the ultrasound beam to a specific depth in the tissue.

As used in the described technique, a beam of ultrasonic energy generated by an ultrasonic transducer may be directed into tissue at an energy level sufficient to excite a nerve, but insufficient to ablate tissue. A distal magnetic sensor may then sense any nerve propagation resulting from the excitation. The transducer may be rotated by a small angle and fired again. A map of points around the circumference that resulted in a magnetometer response may be interpreted as a map of nerve angular locations around the artery. Ablation energy may then be focused at these angles. Following ablation, the excitation ultrasound beam can again be focused at the nerves to verify ablation by no magnetic signal detection. The ultrasonic transducer may be moved to a second or third position along the length of the renal artery, and the procedure repeated.

Magnetometer

Many electrical currents are generated in the body by excitable neural and muscular tissue, and these electrical currents generate magnetic fields. Electrical currents within the body are very small, and the subsequently generated magnetic fields are small as well. As these fields diminish with distance to the source, it is essential to place a magnetosensor as close as possible to pick up a large enough signal. Mapping of both cardiac and brain signals has been widely demonstrated by placing magnetic sensors external to the body. Signals from single nerves being distributed elsewhere in the body have not, however, as the distance from these nerves to an external placed sensor is too large, the signal itself is too low, or the signal is obscured by larger magnetic signals in close proximity (for example the heart signal). External detection of magnetic fields also has to be performed in fully magnetically shielded rooms as magnetic fields from external sources are orders of magnitude larger than those generated by the body. There is therefore a need in a large variety of applications to be able to measure magnetic signals in-vivo using minimal invasive or permanently implantable sensors where one brings the magnetic sensing element as close as possible to the magnetic field source. To give some idea of the strength of these fields, the typical field of a single 10 micrometer nerve axiom at 1 mm distance is on the order of 50 fT. The field oaf a 240 micrometer lateral axon has been found to be on the order of 10 pT at a distance of 1 mm. A nerve ablation catheter with magnetic sensing to identify nerves and assess ablation thus requires a very sensitive magnetometer.

Two types of ultra-sensitive magnetometers presently exist at this moment. One such type of magnetometer is based on quantum interference in atomic vapors. These are commonly referred to as optical magnetometers. Another type utilizes pickup coils operating at a superconductive regime, a so called SQUID (Superconducting Quantum Interference Device). This latter type, however, is not applicable for implantable systems due to the cryogenic temperature requirement.

Optical magnetometers work in a few different regimes, but they have some common principles. The ground state of the electrons in an atom is split into hyperfine Zeeman sublevels by a magnetic field. Spins aligned with the magnetic field have a lower energy level than spins aligned opposite to the field, but among a large population this averages out. A medium can be given a macroscopic magnetic moment by aligning spins of gas atoms in the same direction by a process called optical pumping. If an atom absorbs a photon, the angular momentum of the photon is transferred to the atom because of angular momentum conservation. Using circularly polarized light in which all of the photons have a similar angular momentum (i.e., either left or right circular polarization), the electron can be moved from one of the Zeeman split ground states into an excited state while at the same time changing its magnetic quantum number mF by +1. The electron will decay, but with high probability will stay in the elevated magnetic moment. The gas will send out photons in random direction during the decay process, creating a light appearance of the gas. Repeating this process will finally push the electron into the lowest of the Zeeman split magnetic ground states. The electron cannot be excited from this state, however, because such excitation by the circularly polarized light does not conserve angular momentum of the photon. Thus, the gas cannot any longer absorb the photons and so it becomes dark (i.e., transparent). In this dark state, the electrons are in the lowest energy level among the Zeeman levels, and it is possible for the electrons to switch to higher levels by absorbing energy from an applied radiofrequency field or low level photons. When this occurs, the gas turns back into its non-dark state, and this can be sensed by a change in transmission/absorption of light from, for example, the pumping laser. The shifts in energy level caused by Zeeman splitting are highly specific to the magnetic field with a Q factor over a million. As they are correlated to the magnetic field strength (scalar), the magnetic field can be determined with a very high accuracy by fine tuning the frequency that causes the jump between these Zeeman levels. That is, the RF frequency or photon energy that turns the gas from a dark state to a non-transparent state corresponds to the magnetic field strength.

Another type of magnetometer has been described in which an optical control field causes an optical signal field at a frequency close to a transition frequency incremented by an additional Zeeman splitting energy level to be stored and released by a gas to reveal the strength of the applied magnetic field (see Karpa, *Frequency Matching in Light-Storage Spectroscopy of Atomic Raman Transitions*, Physical Review Letters 103, 093601 (2009)). In this type of magnetometer, referred to herein as a light-storage magnetometer, a mixture of right and left circular polarized beams is used: a pumping beam with one circular polarization direction and a second much weaker signal beam of opposite circular polarization. The signal beam is created having a frequency difference with the first beam which is about equal to the magneto-photo resonance, which corresponds to the energy difference between hyperfine levels due to Zeeman splitting. In a particular implementation, rubidium vapor is used as the sensor gas, and the frequency of the control beam corresponds to the energy difference between an excited state of the rubidium electron and the higher one of the electron's ground states, where the ground state is Zeeman split by the magnetic field to be measured into higher and lower components. The frequency of the signal beam corresponds to the energy difference between the excited state and the lower one of the ground states. In a first step, the medium is optically pumped to drive it to a dark state by depopulating the higher one of the ground states. For example, the control beam may have a left rotating polarization, such that after decay from the |e> state, due to conservation of the rotational momentum, the electron has to move to the |g→ state, and vice versa for signal beam. Because the latter is much smaller in intensity, this forces the gas to end up primarily in the |g→ state. When the Rb medium is irradiated with both the control beam and the lower power signal beam, the latter may be in the form of short pulses to optically pump the medium to the dark state. Both beams are then turned off. Either immediately thereafter or after a short energy storage period (e.g., 0-0.5 ms, preferably less than 50 microseconds), only the control beam is turned back on at low power. The resulting signal detected after transmission through the medium is then an exponentially decaying version of the control beam mixed with the signal beam as regenerated by the medium itself. The oscillation frequency of the detected signal is due to optical beating between the control beam and the regenerated signal beam. This oscillation frequency corresponds to energy difference between the Zeeman split ground stated and, hence, the strength of the magnetic field applied to the Rb medium.

In selecting the frequencies of the control and signal beams to be used before the magnetic field (and hence of the energies of the Zeeman split ground states) is known, the natural linewidth and Doppler broadening has to be considered. One can choose very broad laser frequencies such that there is always an overlap with the specific Zeeman levels and these natural linewidth broadenings. It is also possible to start with a laser fixed at the normal D1 transition without Zeeman splitting and then one uses an opto-acoustic element to drive the frequencies of the control and signal beams. At a given magnetic field strength, the opto-acoustic element scans different frequencies to obtain the dark state. When this is realized, it is known that there is an overlap between the laser pulse frequency and the specific Zeeman level. With a changing magnetic field strength, it is preferable to use a broad-frequency laser pulse.

An explanation for the operation of the light-storage magnetometer just described is as follows. The group velocity of the signal beam is a function of the power level of the control field. A zero control field basically stores the optical field into the atomic state (freezes the pulse). When the control pulse is turned back on, the signal field is released from the medium as the group velocity increases. As the group velocity is a function of the level of the control field, using a very low power control fields to retrieve the signal pulse stretches the effect of the interference beat. Using a high power control field in this retrieval phase would result in a very fast release of the signal memory and a very short beating pulse, making it hard to measure.

In one embodiment of an optical magnetometer used in the ablation catheter, all electronics and optics are embedded in a MEM based device. All the components are reduced to a package that can fit in the catheter. Maintaining the rubidium gas at 80 Celsius so as to be in the vapor state can be accomplished by providing an insulating housing around the whole structure. For example a tubular construction made out of a highly isolating polymer or ceramic (e.g. parylene, or Zyrconium oxide) can be sued. The power and information can be relayed to the magnetometer by wiring along the catheter or by having a battery and wireless communication capability built in.

Figure 4:
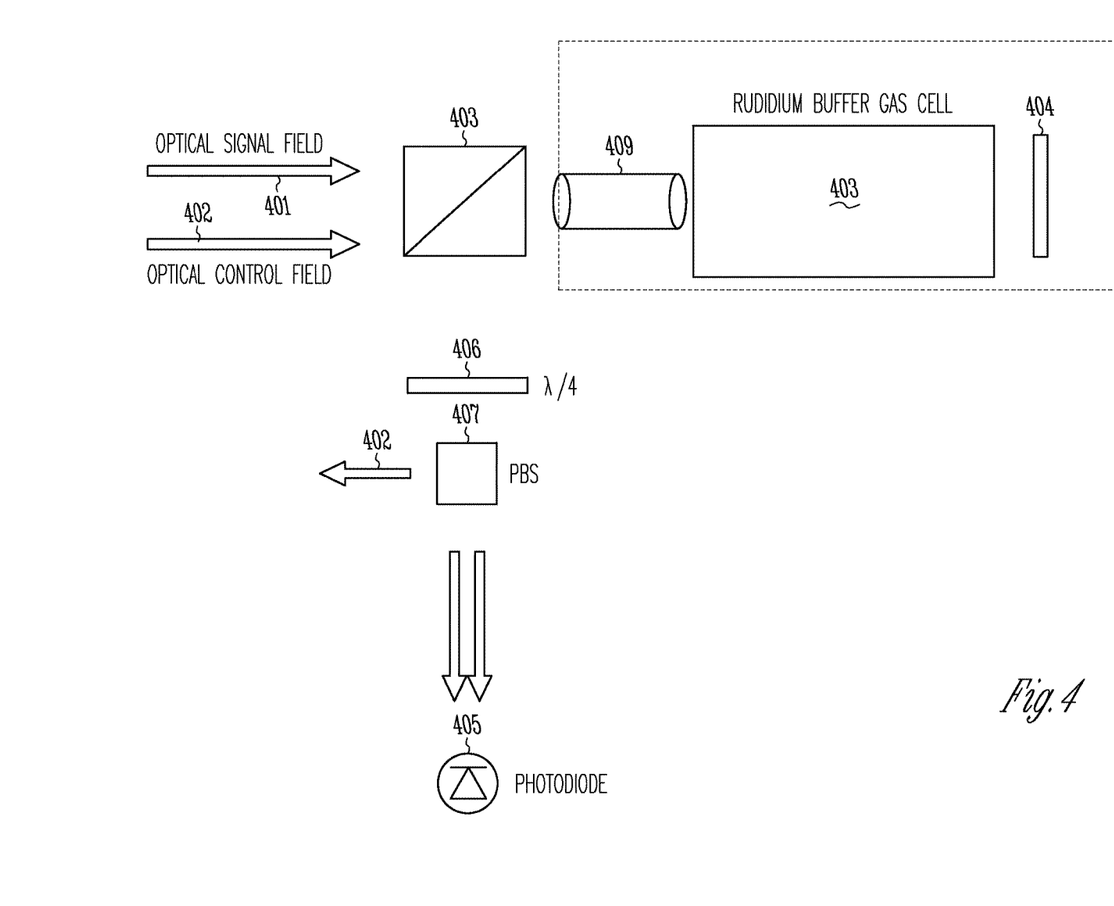
FIG. 4 illustrates a light-storage magnetometer according to one embodiment.

In another embodiment, a fully optical light-storage magnetometer is incorporated into the catheter in which all of the electronics are located externally from the catheter as depicted in FIG. 4. The control beam 401 and signal beam 402 are transmitted from laser sources external to the catheter through a beam splitter 403 to optical fiber 409 within the catheter to the vapor cell 403. In a particular embodiment, a grating stabilized diode laser locked to a wavelength near 795 nm is used a as laser source of both the optical signal as well as the control field. The two beams pass independent acousto-optical modulators to allow for a variation of the difference frequency and intensity of the individual beams. In a particular embodiment, the vapor cell 403 contains rubidium and a neon buffer gas. The mirror 404 incorporated into the end of the vapor cell reflects the light transmitted through the vapor cell back to the beam splitter 403 where it is directed to photodiode 405. Between the beam splitter 403 and photodiode 405 are a quarter wave plate 406 and a polarization maintaining beam splitter 407 for removing the reflected control beam. Only the vapor cell 403, mirror 404, and the optical fiber 409 are located within the catheter as represented by the dashed line. The other components of the magnetometer may be located in the control unit 170 or elsewhere. Such components could include electronic circuitry for controlling the operation of the lasers, receiving and processing signals from the photodiodes, and generation of a waveform signal corresponding to the magnitude of the magnetic field versus time.

Figure 5A:
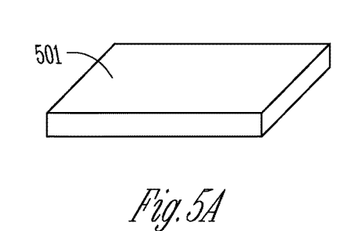
FIGS. 5A through 5F illustrate the etching and anodic bonding steps involved in fabricating a vapor filled cell.
Figure 5B:
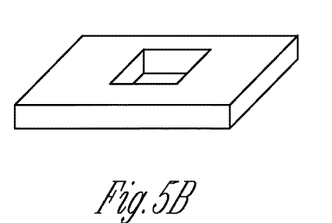
Figure 5C:
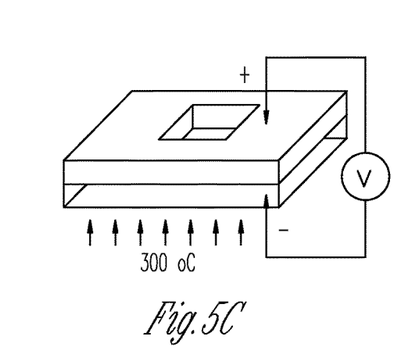
Figure 5D:
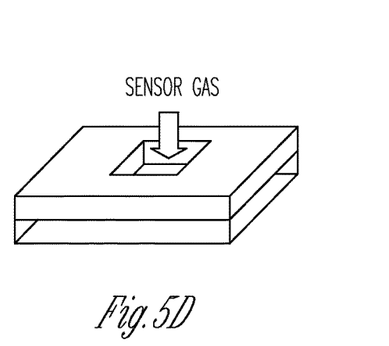
Figure 5E:
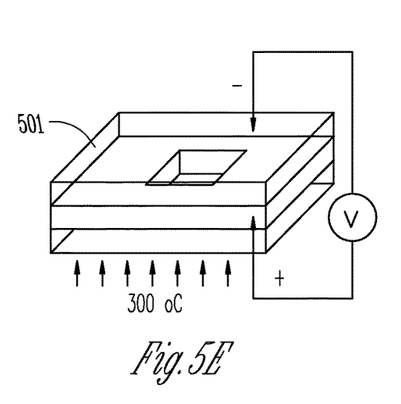
Figure 5F:
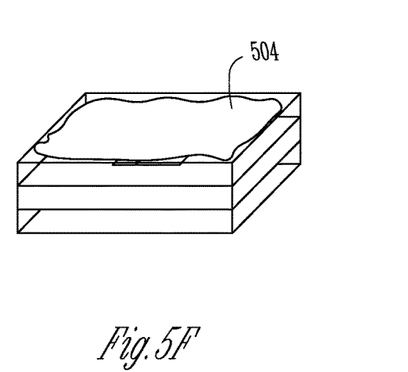
Figure 6:
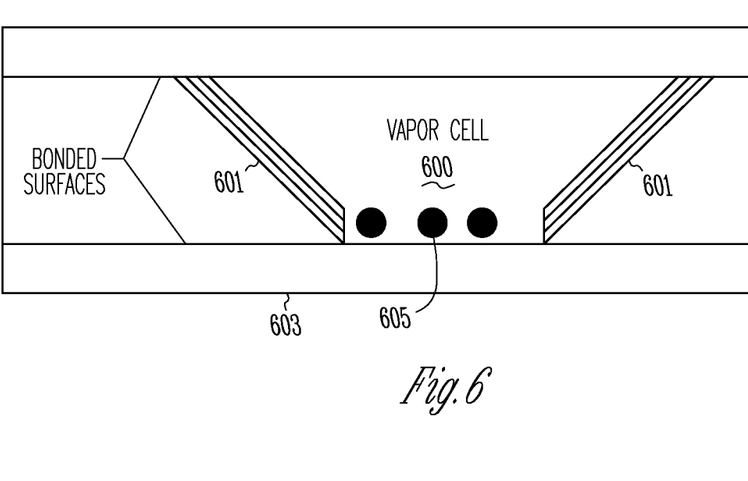
FIG. 6 shows an example gas vapor cell.

To construct a magnetometer such as illustrated in FIG. 4 or according to other particular embodiments, a rubidium gas vapor cell is attached to an optical fiber. One technique for producing microfabricated vapor filled cells is based on etching and anodic bonding (See Liew, *Microfabricated alkali atom vapor cells*, Applied Physics Letters Volume 84, No. 14, 5 Apr. 2004). The etching and anodic bonding steps involved in fabricating a vapor filled cell are illustrated by FIGS. 5A through 5F. A cavity 502 is formed within a substrate 501 for containing the gas, and a Pyrex glass window 503 is anodically bonded to both sides of the substrate. Such gas cells could be filled with various suitable vapors (e.g., rubinium, cesium, kalium) and buffer gases such as nitrogen. Anodic bonding of the glass optical fiber to the glass cell could be done using one of various intermediate layers such as silicon carbide, silicon nitride, polysilicon, silicon dioxide, amorphous silicon, or hydrogenated amorphous silicon. The thickness of the material needed ranges from 800 Angstrom to 5000 Angstrom. A gold coating 504 may be affixed to the top Pyrex glass window to produce a mirror. Another alternative would be to include a mirror structure 601 in the gas vapor cell 600 as illustrated in FIG. 6 (see Perez, Rubium Vapor Cell With Integrated Nonmetallic Multilayer Reflectors, MEMS 2008, Tucson, Ariz., USA, Jan. 13-17, 2008). Yet another alternative is to combine a hollow core waveguide filled with the alkali gas with a solid core system (see Wu, *Planar Hollow-Core Waveguide Technology for Atomic Spectroscopy and Quantum Interference in Alkali Vapors*, Journal of Lightwave Technology, Vol. 26, No. 23, Dec. 1, 2008). The glass optical fiber to deliver the optical beams could then be bonded by anodic bonding to this structure.

As noted above, to function as a sensor gas in a magnetometer, the rubidium (or other element) must be maintained in a vapor state. For rubidium, this means that the rubidium must be heated to 80 degrees Celsius. Although the embodiment illustrated by FIG. 5 is without RF activation and requires only one optical fiber and a gas filled vapor cell in the catheter, the rubidium still needs to be heated. Electric heating is possible, but a preferred system would be to use the same optical fiber to provide the heating. Metal nanoparticles exposed to incident laser irradiation at wavelengths close to the surface plasmon resonance efficiently couple the optical energy and generate heat. Light absorption and heat generation of gold nanoparticles is very frequency dependent, but as well very effective near the optimum frequency. In other words, a pulsed laser beam is delivered at a different frequency band (around 532 nm) than the two optical pumping and probing beams as described above which operate at 795 nm to heat the vapor cell. The gold nanoparticles 605 would be coated on the bottom Pyrex window 603 as shown in FIG. 6 before bonding anodically bonding the Pyrex to vapor cell.

Magnetic Shielding

The renal nerve ablation procedure as described above may need to be done in a room shielded against the static earth magnetic field that is around 0.5 Gauss, as well as against low and high frequency magnetic fields produced by electronic equipment. The former is established by covering the measurement space (room) using high-permeability foils (in single or multiple layers with spacing) that are commercially available. Shielding against higher frequency can be achieved using foils including high conductivity materials. However, if the optical magnetic sensor has a large enough dynamic range, so that nerve signals that arise in a given frequency band are larger than noise in that band, a band pass filter may be used to eliminate the Earth's magnetic field and higher frequency signals from interfering sources. In addition, two magnetometers may be configured in a gradiometer configuration to eliminate static fields such as the Earth's field that do not vary appreciably over the base line of the gradiometer. For example, in the case of magnetic field sensing from a catheter placed at the center of the renal artery separated by 5 mm from the nerve, the difference in magnetic field sensed by two identical atomic magnetometers placed 5 mm apart on the catheter would cancel static magnetic fields while sensing the nerve signal at it passes over each of the magnetometers. The two magnetometers would need to be separated by a rigid structure. The combination of a gradiometer configuration and band-pass filtering may obviate the need for a magnetically shielded environment.

Other Applications

The magnetometer embodiments as described herein may have a large variety of applications where it is necessary to measure magnetic signals in-vivo using minimal invasive or permanently implantable sensors and where the magnetic sensing element can be brought close to the source of magnetic field. Such applications may include: 1) detection of foreign magnetic material such as magnetic nano-particles which might have been injected together with a tracer or active drug component to reveal, for example, cancerous tissue, 2) as a receiver element to sense information which can be relayed to implanted devices such as a magnetic sensor (antenna) attached to a pacemaker to receive information), 3) as an internal pickup sensor for externally induced magnetic fields such as NMR fields, 4) to measure flow in either fluid or air environments (e.g., blood, urine, or air) where the medium has been enriched with magnetic particles. Besides just detecting biomagnetic fields and using this information to re-construct the two or three dimensional current distribution in the heart or other organ, procedures could also be performed whereby an invasive procedure is undertaken while the effect is directly being monitored using magnetic fields. For example, in the case where a nerve is being transected or ablated, one could measure the nerve activity to see that no activity is present as proof for the success of the operation. In the case of a nerve reattachment procedure, the nerve activity could be monitored to ascertain that the nerve is functional.

Embodiments relating to further particularizations and features have been described above. It should be appreciated that those embodiments may also be combined in any manner considered to be advantageous. Also, many alternatives, variations, and modifications will be apparent to those of ordinary skill in the art. Other such alternatives, variations, and modifications are intended to fall within the scope of the following appended claims.

What is claimed is:

1. A method, comprising:
   disposing a magnetometer adjacent selected nervous tissue and producing a magnetometer signal therefrom;
   disposing an ablation instrument adjacent the selected nervous tissue, where the ablation instrument may be operated in either a low-power stimulation mode that stimulates the nervous tissue without destroying the nervous tissue or a high-power ablation mode that destroys the nervous tissue, wherein the low-power stimulation mode and the high-power ablation mode are defined by a specified threshold power level, below which results in stimulation of the nervous tissue and above which results in ablation of the nervous tissue, and wherein the magnetometer signal is correlatable with a time at which stimulation of the nervous tissue is delivered;
   analyzing the magnetometer signal while repeatedly delivering low-power stimulation from the ablation instrument;
   determining that energy from the ablation instrument is directed toward the selected nervous tissue if a change occurs in the magnetometer signal that is time-correlated with the delivery of low-power stimulation for a predetermined threshold number of times as the delivery of low-power stimulation is repeated; and,
   if it is determined that energy is directed toward the selected nervous tissue, switching the ablation instrument to ablation mode to destroy the selected nervous tissue.

2. The method of claim 1 further comprising adjusting the location or orientation of the ablation instrument until it is determined that energy is directed toward the selected nervous tissue.

3. The method of claim 1 wherein the magnetometer is a vapor cell containing a sensor gas to which light is transmitted and reflected therefrom and further wherein the vapor cell is incorporated into a catheter with fiber optic cable running through one or more lumens of the catheter for transmitting and receiving light to and from the vapor cell.

4. The method of claim 3 further comprising heating the sensor gas using light transmitted by the fiber optic cable.

5. A method, comprising:
   guiding a catheter that comprises a tube having proximal and distal ends to selected nervous tissue;
   actuating an ablation instrument near the distal end of the catheter in a low-power mode designed to stimulate nervous tissue without destroying the nervous tissue;
   sensing a magnetic field at a region near the distal end of the catheter, wherein the magnetic field that is sensed is correlatable with a time at which stimulation of the nervous tissue is delivered;
   determining from the sensed magnetic field that the low-power actuation of the ablation instrument resulted in stimulation of the selected nervous tissue if a change in the sensed magnetic field that is time-correlated with actuation of the ablation instrument is detected for a predetermined threshold number of times as the low-power actuation is repeated;
   if the low-power actuation of the ablation instrument results in stimulation of the selected nervous tissue, actuating the ablation instrument in a high-power mode to destroy the tissue; and,
   wherein the low-power mode and the high-power mode are defined by a specified threshold power level, below which results in stimulation of the nervous tissue and above which results in ablation of the nervous tissue.

6. The method of claim 5 further comprising moving the catheter until the low-power actuation of the ablation instrument results in stimulation of the selected nervous tissue.

7. The method of claim 5 wherein the catheter is intravascularly guided to a renal artery and wherein renal sympathetic nerves surrounding the renal artery are the selected nervous tissue.

8. The method of claim 5 wherein the sensing of the magnetic field is performed with an optical magnetometer.

9. The method of claim 8 wherein the sensing of the magnetic field is performed with a light-storage magnetometer that includes a vapor cell for containing a sensor gas, a mirror, and optical fiber located within the catheter.

10. The method of claim 9 further comprising heating the sensor gas within the vapor cell of the magnetometer with laser light delivered by optical fiber within the catheter.

11. A device for monitoring nerve activity, comprising:
    a vapor cell containing a sensor gas disposable adjacent selected nervous tissue;

a mirror structure in the vapor cell;
a laser source for generating light at selected frequencies;
optical fiber for transmitting light from the laser source to the vapor cell and receiving light reflected therefrom;
circuitry for controlling the light transmission so that the vapor cell operates as a light-storage magnetometer with the reflected light having a frequency component that corresponds to the magnitude of the magnetic field at the location of the sensor gas;
circuitry for processing the received light to measure the magnetic field at the location of the sensor gas;
an ablation instrument disposable adjacent the selected nervous tissue, wherein the ablation instrument may be operated in either a low-power stimulation mode that stimulates nervous tissue without destroying the nervous tissue or a high-power ablation mode that destroys nervous tissue, wherein the low-power stimulation mode and the high-power ablation mode are defined by a specified threshold power level, below which results in stimulation of the nervous tissue and above which results in ablation of the nervous tissue and wherein the magnetic field that is measured is correlatable with a time at which stimulation of the nervous tissue is delivered;
a control unit having processing circuitry for determining that energy from the ablation instrument is directed toward the selected nervous tissue by detecting a change in the measured magnetic field that is time-correlated with the delivery of low-power stimulation from the ablation instrument for a predetermined threshold number of times as the delivery of low-power stimulation is repeated;
wherein the control unit is configured to determine that energy from the ablation instrument is directed toward the selected nervous tissue if a change occurs in the magnetometer signal that is time-correlated with the delivery of low-power stimulation for a predetermined threshold number of times as the delivery of low-power stimulation is repeated; and, if it is determined that energy is directed toward the selected nervous tissue, switching the ablation instrument to ablation mode to destroy the selected nervous tissue.

12. The device of claim 11 wherein the ablation instrument is configured to produce a focused beam using two or more irradiative elements that allows a relative phase between radiated waves to be adjusted.

13. An apparatus, comprising:
a catheter that comprises a tube having proximal and distal ends;
an ablation instrument near the distal end of the catheter, wherein the ablation instrument may be operated in a low-power mode to stimulate nervous tissue without destroying the nervous tissue or operated in a high-power mode to destroy nervous tissue, wherein the low-power mode and the high-power mode are defined by a specified threshold power level, below which results in stimulation of the nervous tissue and above which results in ablation of the nervous tissue;
a magnetic sensor near the distal end of the catheter configured to sense magnetic fields produced as a result of stimulation of nervous tissue by the ablation instrument, wherein the magnetic field that is measured is correlatable with a time at which stimulation of the nervous tissue is delivered;
a control unit having processing circuitry for actuating the ablation instrument and analyzing signals from the magnetic sensor; and,
wherein the control unit is configured to determine that energy from the ablation instrument is directed toward selected nervous tissue so that the selected nervous tissue can be destroyed, by repeatedly delivering low-power stimulation from the ablation instrument a specified number of times and determining that a feature in the magnetic sensor signal consistently occurs at the same time that the low-power stimulation is delivered.

14. The apparatus of claim 13 wherein the catheter further comprises a gold marker for radiographically locating the catheter.

15. The apparatus of claim 13 further comprising a bandpass filter for passing magnetic sensor signals corresponding to nerve activity and blocking noise signals.

16. The apparatus of claim 13 wherein the magnetic sensor comprises two magnetometers configured in a gradiometer configuration to eliminate static fields.

17. The apparatus of claim 13 wherein the ablation instrument is configured to produce a focused beam using two or more irradiative elements that allows a relative phase between radiated waves to be adjusted.

18. The apparatus of claim 17 wherein the magnetic sensor is an optical magnetometer.

19. The apparatus of claim 18 wherein the magnetic sensor is a light-storage magnetometer.

20. The apparatus of claim 19 wherein the magnetic sensor includes a vapor cell for containing a sensor gas, a mirror, and optical fiber located within the catheter.

21. The apparatus of claim 18 wherein the magnetometer includes a vapor cell with a cavity formed within a hollow core waveguide filled with the sensor gas that is bonded to optical fiber.

22. The apparatus of claim 18 wherein the magnetometer includes a vapor cell for containing a sensor gas and wherein the vapor cells includes particles that are heated by laser light delivered to the vapor cell by optical fiber.

23. The apparatus of claim 22 wherein the particles are gold nanoparticles.

24. The apparatus of claim 18 wherein the magnetometer includes a vapor cell with a cavity formed within a substrate for containing the sensor gas and a glass window anodically bonded to both sides of the substrate.

25. The apparatus of claim 24 further comprising a gold coating affixed to the top glass window to provide a mirror.

26. The apparatus of claim 24 wherein the vapor cell contains a mirror structure within the cavity.

* * * * *